United States Patent
Ko et al.

(10) Patent No.: US 8,119,116 B2
(45) Date of Patent: *Feb. 21, 2012

(54) THERAPEUTICS FOR CANCER USING 3-BROMOPYRUVATE AND OTHER SELECTIVE INHIBITORS OF ATP PRODUCTION

(75) Inventors: Young Hee Ko, Owings Mills, MD (US); Jean-Francois Geschwind, Potomac, MD (US); Peter L. Pedersen, Columbia, MD (US)

(73) Assignee: John Hopkins University School of Medicine, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/355,115

(22) Filed: Jan. 16, 2009

(65) Prior Publication Data

US 2009/0326068 A1 Dec. 31, 2009

Related U.S. Application Data

(63) Continuation of application No. 10/243,550, filed on Sep. 13, 2002, now Pat. No. 7,547,673.

(60) Provisional application No. 60/318,710, filed on Sep. 13, 2001.

(51) Int. Cl.
*A61K 38/21* (2006.01)
*A61K 31/22* (2006.01)
*A61K 33/24* (2006.01)
*A61K 31/437* (2006.01)
*A61P 35/00* (2006.01)
*C12Q 1/02* (2006.01)
*C12Q 1/48* (2006.01)

(52) U.S. Cl. ....... 424/85.7; 514/550; 514/283; 424/649; 435/29; 435/15

(58) Field of Classification Search .................. 424/85.7, 424/649; 514/550, 283; 435/29, 15
See application file for complete search history.

(56) References Cited

U.S. PATENT DOCUMENTS

| | | | | |
|---|---|---|---|---|
| 4,337,760 | A | * | 7/1982 | Rubin ........................... 604/500 |
| 4,536,387 | A | | 8/1985 | Sakamoto et al. |
| 5,213,804 | A | * | 5/1993 | Martin et al. ................. 424/450 |
| 5,759,547 | A | | 6/1998 | Maione |
| 5,759,837 | A | * | 6/1998 | Kuhajda et al. ............... 435/193 |
| 5,854,067 | A | | 12/1998 | Newgard et al. |
| 6,284,786 | B1 | | 9/2001 | Casciari et al. |
| 6,312,662 | B1 | | 11/2001 | Erion et al. |
| 6,448,030 | B1 | | 9/2002 | Rust et al. |
| 6,670,330 | B1 | * | 12/2003 | Lampidis et al. .............. 514/23 |
| 2001/0046997 | A1 | | 11/2001 | Abraham et al. |
| 2002/0006915 | A1 | | 1/2002 | Mack Strong et al. |
| 2002/0068711 | A1 | | 6/2002 | Pedersen et al. |
| 2003/0018166 | A1 | | 1/2003 | Sacchettini et al. |
| 2003/0087961 | A1 | | 5/2003 | Ko et al. |
| 2003/0139331 | A1 | | 7/2003 | Martin et al. |
| 2004/0029826 | A1 | | 2/2004 | Sokoloff et al. |
| 2004/0167079 | A1 | | 8/2004 | Tidmarsh |
| 2004/0167196 | A1 | | 8/2004 | Tidmarsh |
| 2006/0154867 | A1 | | 7/2006 | Sokoloff et al. |

FOREIGN PATENT DOCUMENTS

WO     WO-97/04104 A2     2/1997

OTHER PUBLICATIONS

Fiebig et al., "Relevance of Tumor Models for Anticancer Drug Development", Contrib. Oncol. Basel. Karger, vol. 54, pp. 109-120 (1999).*
Chemical Abstracts 124:193528, "Phase I clinical and pharmacokinetic study of leucovorin and infusional hepatic arterial fluorouracil", Kerr et al. (1995).*
Arafat et al., "Toxicities Related to intraarterial infusion of Cisplatin and Etoposide in Patients with Brain Tumors," J. of Neuro-oncology, 42:73-77 (1999).
Bar et al., "Sorbitol Removal by the Metastatic Liver: A Predictor of Systemic Toxicity of Intra-arterial Chemotherapy in Patients with Liver Metastases," J. of Hepatology, 30:1112-1118 (1999).
Fiebig et al., "Relevance of Tumor Models for Anticancer Drug Development," Contrib. Oncol. Basel. Karger, 54:109-120 (1999).
Geschwind et al., "Novel Therapy for Liver Cancer: Direct Intraarterial Injection of a Potent Inhibitor of ATP Production," Cancer Research, 62:3909-3913 (2002).
Gobin et al., "Intraarterial Chemotherapy for Brain Tumors by Using a Spatial Dose Fractionation Algorithm and Pulsatile Delivery," Radiology, 218(3):724-732 (2001).
Johns Hopkins Medical Institutions Office of Communications and Public Affairs "Energy Blocker May Be Potential Liver Cancer Treatment," www.hopkinsmedicine.org/press/2002/July020715.htm.
Kerr et al., "Phase I Clinical and Pharmacokinetic Study of Leucovorin and Infusional Hepatic Arterial Flurouracil," J. of Clinical Oncology, 13(12):2968-2972 (1995).
Ko et al., "Advanced Cancers: Eradication in All Cases Using 2-bromopyruvate Therapy to Deplete ATP," BBRC, 324(1):269-275 (2004).
Ko et al., "Advanced Cancers: Eradication in All Cases Using 3-bromopyruvate Therapy to Deplete ATP," Press Release, Nov. 5, 2004.

(Continued)

*Primary Examiner* — Jeffrey S. Lundgren
*Assistant Examiner* — Zohreh Vakili
(74) *Attorney, Agent, or Firm* — Foley Hoag LLP

(57) ABSTRACT

The present invention relates to methods of treating a cancerous tumor using selective inhibitors of ATP production. The present invention also relates to pharmaceutical preparations comprising such inhibitors and methods for administering them intraarterially directly to a tumor, as well as methods for identifying compositions that selectively inhibitor ATP production for use in the invention.

12 Claims, 7 Drawing Sheets

OTHER PUBLICATIONS

Ko et al., "Metabolic Properties of the Rabbit VX2 Tumor Model Following Liver Implantation: Role for Hexokinase," Cancer Research, 42:519 (2001).

Ko et al., "Glucocatabolism in the Rabbit VX2 Tumor Model for Liver Cancer: Characterization and Targeting Hexokinase," Cancer Letters, 173:83-91 (2001).

Kostron et al., "Photodynamic Treatment of Malignant Brain Tumors," Jg 102, Heft 18:531-535 (1990).

Lin et al., "Effects of 90Y-Microspheres on Livers Tumors: Comparison of Intratumoral Injection Method and Intra-Arterial Injection Method," The J. of Nuclear Medicine, 41(11):1892 (2000).

Mathupala et al., "Glucose Catabolism in Cancer Cells," The J. of Biological Chemistry, 276(46):43407-43412 (2001).

Pederson, P., ""Energy Blocker" Kills Big Tumors in Rats," Audio File—Johns Hopkins Medicine, Office of Corporate Communications, Oct. 14, 2004.

Pedersen et al., "Mitochondrial Bound Type II Hexokinase: a Key Player in the Growth and Survival of Many Cancers and an Ideal Prospect for Therapeutic Intervention," Biochimica and Biophysics Acta, 1555:14-20 (2002).

Soulen et al., "Intraarterial Chemotherapy with Limb-sparing Resection of Large Soft-tissue Sarcomas of the Extremities," JVIR, 3:659-663 (1992).

Wang et al., "Isolated Lower Extremity Chemotherapeutic Infusion for Treatment of Osteosarcoma: Experimental Study and Preliminary Clinical Report," J. Vasc. Interv. Radiol., 12:731-737 (2001).

Higashi, T. et al., "Relationship Between Retention Index in Dual-Phase 18F-FDG PET, and Hexokinase-II and Glucose Transporter-1 Expression in Pancreatic Cancer," J Nucl Med, 43:173-180 (2002).

Miccoli, L. et al., "Intracellular pH Governs The Subcellular Distribution of Hexokinase in a Glioma Cell Line," Biochem. J., 313:957-962 (1996).

Minn, H. et al., "Determination of 2-fluoro-2-deoxy-D-Glucose Uptake and ATP Level for Evaluating Drug Effects in Neoplastic Cells," Res Exp Med, 191:27-35 (1991).

Nelson, K. et al., "3-Bromopyruvate Kills Cancer Cells in Animals," The Lancet Oncology, 3(9):524 (2002), Abstract Only.

Yamada, K. et al., "Factors Influencing [F-18] 2-Fluoro-2-Deoxy-D-Glucose (F-18 FDG) Uptake in Melanoma Cells: The Role of Proliferation Rate, Viability, Glucose Transporter Expression and Hexokinase Activity," The J. of Dermatology, 32:316-334 (2005).

International Search Report for PCT/US2007/087740 mailed on Jun. 3, 2008.

International Search Report for PCT/US2009/004789 mailed on May 3, 2010.

* cited by examiner

THERAPEUTICS FOR CANCER USING 3-BROMOPYRUVATE AND OTHER SELECTIVE INHIBITORS OF ATP PRODUCTION

RELATED APPLICATIONS

This application is a continuation of U.S. application Ser. No. 10/243,550, filed on Sep. 13, 2002, which claims the benefit of priority under 35 U.S.C. §119(e) to Provisional Application Ser. No. 60/318,710, filed Sep. 13, 2001, the contents of which are all incorporated by reference in their entirety herein.

GOVERNMENT SUPPORT

The subject invention was made in part with support from the U.S. Government under a grant (CA 80118) from the National Institutes of Health. Accordingly, the U.S. Government has certain rights in this invention.

BACKGROUND OF THE INVENTION

One of the most common, profound, and intriguing phenotypes of highly malignant tumors, known for more than six decades, is their ability to metabolize glucose at high rates to synthesize high levels of ATP. Under aerobic conditions more than half of the ATP produced in such tumor cells is derived via glycolysis, in sharp contrast to normal cells, where this value is usually less than 10% and oxidative phosphorylation is the predominant method for ATP generation. Under hypoxic (low oxygen tension) conditions, frequently present within tumors, the already high glycolytic rate may double, allowing the tumor cells to thrive while neighboring normal cells become growth deficient. This is a characteristic of both animal and human tumors including those derived from brain, breast, colon, liver, lung, and stomach. In each, a close correlation exists among the degree of de-differentiation, growth rate, and glucose metabolism, where the most de-differentiated tumors exhibit the fastest growth and the highest glycolytic rate. In fact, this unique phenotype is used clinically worldwide in Positron Emission Tomography (PET) to detect tumors, assess their degree of malignancy, and in some, cases even predict survival time.

Despite the commonality of the high glycolytic phenotype and its widespread use clinically as a diagnostic tool, it has not been exploited as a major target for arresting or slowing the growth of cancer cells because the underlying molecular basis of the high glycolytic phenotype is not completely characterized. It had long been suspected to involve some type of mitochondrial glycolytic interaction. Recent experiments have demonstrated a requirement for an overexpressed mitochondrially bound form of hexokinase, now identified as Type II hexokinase.

Liver cancer, in particular hepatocellular carcinoma (hepatoma), is one of the most common fatal cancers in the world and soon may reach epidemic levels due to increased incidences of virally-induced hepatitis. Among its numerous victims are not only those with primary tumors that develop directly in the liver but those with secondary tumors that frequently arise in this critical metabolic organ as a result of metastasis from other tissues, e.g., the colon. Unfortunately, traditional treatment options are limited by poor response rates, severe toxicities, and high recurrence rates resulting in a mean survival time of about 6 months. Hepatomas are known to exhibit a high glucose catabolic rate, and where examined carefully, to contain elevated levels of hexokinase bound to their mitochondria. Moreover, in the AS-30D hepatoma, the most extensively studied tumor in this class, it has been shown also that the gene for hexokinase is amplified and that the mRNA levels are markedly elevated. Therapeutic methods directed at inhibition of metabolic activity in hepatoma are limited by the fact that a potent agent directed at any of the metabolic enzymes such as hexokinase in the tumor will also target the patient's metabolic enzymes, resulting in severe toxicity. Thus, less potent, but very specific agents such as antisense molecules, have been used to inhibit tumor metabolic activity.

In recent years, the VX2 tumor, an epidermoid rabbit tumor induced by the Shope papilloma virus, has shown promise as a model system for studying hepatoma. The VX2 tumor grows well when implanted in the rabbit's liver, where it takes on growth properties and a vascularization system similar to many human liver tumors. Thus, it is possible via the method known as transcatheter chemoembolization to deliver anticancer agents directly to the implanted tumor via the hepatic artery. In addition, it has been shown that when delivery is made using certain oils the mixture preferentially localizes in the tumor rather than in the surrounding liver tissue. This is important as it may allow for the targeting of exceptionally potent cancer killing agents directly to the tumor for brief periods of time thus minimizing damage to the surrounding liver tissue and toxicity to the host. The energy metabolism of the VX2 tumor requires further characterization in order to determine to what extent it mimics a rapidly growing hepatoma (e.g. exhibits a high glycolytic phenotype, expresses mitochondrially bound hexokinase, etc.).

SUMMARY OF THE INVENTION

The present invention provides in part therapeutic compositions comprising and methods of treating cancer using 3-bromopyruvate and other selective inhibitors of ATP production.

In a preferred embodiment, the invention further provides inhibitors of ATP production represented in general formula:

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate is selected from the group consisting of: triflate, mesylate and tosylate. In yet another embodiment, X is an amine oxide is dimethylamine oxide.

In another aspect, the invention provides selective inhibitors of ATP production represented in the general formula:

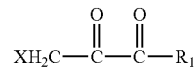

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain other embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate is selected from the group consisting of: triflate, mesylate and tosylate. In yet another embodiment, X is an amine oxide is dimethylamine oxide. In certain embodiments $R_1$ represents OR, H, $N(R'')_2$, C1-C6 alkyl, C6-C12 aryl, C1-C6 heteroalkyl, or a C6-C12 heteroaryl. Independently, in other embodiments, R'' represents H, C1-C6 alkyl, or C6-C12 aryl. Independently, in still other embodiments, R represents H, alkali metal, C1-C6 alkyl, C6-C12 aryl or C(O)R'; and R' represents H, C1-C20 alkyl or C6-C12 aryl.

In another aspect, the present invention provides, in part, methods for screening candidate selective inhibitors of ATP production using at least a portion of VX2 tumor. Thereby, the invention provides methods for identifying additional selective inhibitors of ATP production for use in the instant invention. Such methods may comprise assaying the ability of a candidate inhibitor to modulate the activity of an enzyme in a pathway involved in ATP production in a tumor slice, whole tumor, cell derived from a tumor, and the like. Pathways involved in ATP production may be selected from such exemplary pathways as glycolysis and mitochondrial respiration.

The present invention further provides pharmaceutical compositions comprising the subject inhibitors. In certain embodiments, the pharmaceutical composition preferably comprises one or more of the inhibitors and a pharmaceutically acceptable carrier. In certain embodiments, the pharmaceutical composition comprises a 3-halopyruvate. In one embodiment, pharmaceutical composition comprises 3-bromopyruvate. In still other embodiments, the pharmaceutical composition comprises one or more of the inhibitors, a second chemotherapeutic agent, and optionally a pharmaceutically acceptable carrier. In yet another embodiment, the pharmaceutical composition comprises one or more of the inhibitors, a scavenger compound, and optionally a pharmaceutically acceptable carrier.

The present invention further provides novel therapeutic methods of treating a cancerous tumor comprising administering to the subject an effective amount of a subject pharmaceutical composition comprising an effective amount of a selective inhibitor of ATP synthesis. In certain embodiments, the method comprises parenterally administering a subject composition to a subject. In one embodiment, the method comprises intraarterial administration of a subject composition to a subject. In one embodiment, the method comprises administering an effective amount of a subject composition directly to the arterial blood supply of the cancerous tumor. The intraarterial delivery of the ATP synthesis inhibitor directly to the blood supply of the tumor may be done in conjunction with emobilization of the tumor (i.e. i.e. occluding (closing), or at least drastically reducing, blood flow to one or more blood vessels supplying the tumor)—i.e. "chemoembolization." In a preferred embodiment, the ATP synthesis inhibitor is administered directly to the blood supply of the tumor without embolization of the tumor.

In one preferred embodiment, the cancerous tumor is a liver tumor. In still other embodiments, the method comprises systemic administration of a subject composition to a subject. In certain embodiments, the methods of treating a cancerous tumor comprise administering a subject inhibitor and administering a second agent to a subject. Such administration may be simultaneous or sequential. In one embodiment, the second agent is a chemotherapeutic agent. In another embodiment, the second agent is a scavenger compound. In certain embodiments, the second agent may be formulated into a separate pharmaceutical composition. In other embodiments, the inhibitor and second agent are co-formulated into a pharmaceutical composition.

In other embodiments, this invention contemplates a kit including subject pharmaceutical compositions, and optionally instructions for their use. Uses for such kits include, for example, therapeutic applications. In certain embodiments, the subject compositions contained in any kit have been lyophilized and require rehydration before use.

Other features and advantages of the invention will be apparent from the following detailed description, and from the claims.

BRIEF DESCRIPTION OF THE FIGURES

FIG. 1A depicts an excised VX2 tumor after 4 weeks growth in the rabbit hind limb. FIG. 1B depicts a control liver isolated from a rabbit of the same age. FIGS. 1C and 1D depict livers harboring, respectively, VX2 tumors after 4 and 5.7 weeks of implantation.

In FIG. 4A, the control, almost all cells in the field are viable as indicated by a dark nucleus and a surrounding bright appearing cytosol. Where indicated, 20 mM 2DOG (FIG. 4B) or 5 mM 3BrPA (FIG. 4C) were added to cells that had been growing for 24 hours. After an additional 12 hours, the viability of the cells was assessed as described in the Exemplification using trypan blue. The remaining viable cells in FIG. 4B (2DOG) are indicated by arrows. In FIG. 4C, (3BrPA) there are no such cells as they have all taken up the trypan blue.

FIG. 5A depicts a schematic of tumor implantation and growth. FIG. 5B depicts two representative hepatic arteriograms. Each shows the hepatic artery leading into a highly vascularized tumor (circled) located within the left lobe. FIG. 5C depicts a histological section of a control "untreated" liver implanted tumor isolated 4 days after intraarterial injection of only a saline solution. This section obtained from a region of the tumor located outside the necrotic tumor core shows almost all viable cells. (Magnification=640×) FIG. 5D depicts sections of a liver implanted tumor isolated 4 days after intraarterial injection of 3-BrPA. This section obtained from the same location of the tumor as the control shows no viable cells. (Magnification=640×) FIG. 5E depicts sections from a 3-BrPA treated tumor identical to that in FIG. 5D but showing a region near an artery (arrow) where a tiny cluster of cells remains viable. (Magnification=640×) FIGS. 5F and 5G depict sections from the liver of a control "untreated" animal and from the liver tissue surrounding an implanted tumor that had been injected intrarterially with 3-BrPA. In both, all cells are viable. (Magnification=120×). FIG. 5H depicts a bar graph summarizing the killing efficacy of intraarterial 3-BrPA on liver tumors. Data are plotted as the mean±standard deviation. For the liver samples, there was no standard deviation as all cells tested viable.

FIG. 6A depicts a view of the left hepatic artery observed microscopically after injection of embolization material (polyvinyl alcohol) and Ethiodol to block blood flow to the liver (5). (Magnification=120×). FIG. 6B depicts embolized livers harboring VX2 implanted tumors (circles). Arrows indicate damage 4 days after embolization. FIG. 6C depicts a liver isolated 4 days after its implanted VX2 tumor (circle) received a single injection of 3-BrPA. There is no sign of liver damage. FIG. 6D depicts histological sections from those regions of livers shown in B that had been affected by embolization. Some tissue has suffered severe damage (nonviable region) and some has remained viable. (Magnification=120×). FIG. 6E depicts sections of 8 tissues from an animal harboring a liver implanted VX2 tumor treated by intraarterial injection of 3-BrPA. All tissues exhibit a normal staining pattern. (Magnification=120×). FIG. 6F depicts sections derived from the same animal showing "metastatic" lung tumors. (Magnification=120×).

FIG. 7A depicts histological sections of 9 different tissues isolated 4 days after injecting 3-BrPA (25 ml 0.5 mM) into a marginal ear vein. No damage to these tissues is evident. (Magnification=120×). FIG. 7B depicts a section from a liver implanted VX2 tumor isolated from a control animal not receiving 3-BrPA. FIG. 7C depicts a comparable sample from an animal receiving 3-BrPA systemically. Cells in both appear completely viable. (Magnification 120×) FIG. 7D depicts a section of lung tissue isolated from an animal in which the liver harbored a VX2 tumor after 14 days of growth. FIG. 7E depicts a comparable section isolated from the lung of an identical animal 4 days after receiving a systemic injection of 3-BrPA. (Magnification=64×) The growth of "metastatic" tumors has been markedly suppressed. FIG. 7F depicts a bar graph emphasizing that, of the total number of "metastatic" lung tumors counted (>27) in comparable histological sections, 5 were greater than 1 mm in diameter in untreated animals harboring a liver implanted VX2 tumor, and none were greater than 1 mm in identical animals that received 3-BrPA systemically. (Animals evaluated=4).

DETAILED DESCRIPTION OF THE INVENTION

1. Definitions

Figure 1:
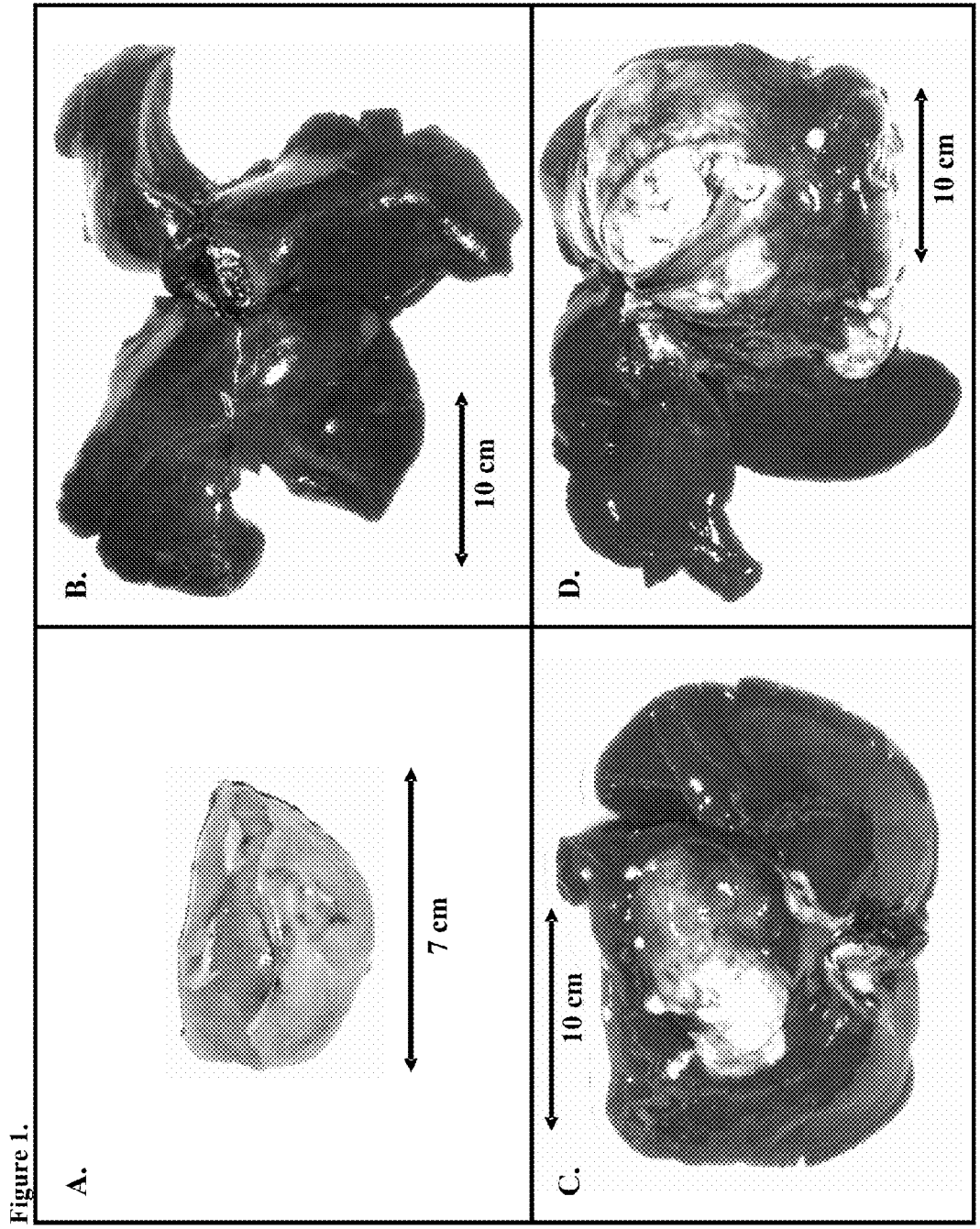
FIG. 1 depicts photographs of a VX2 tumor.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The terms "library" or "combinatorial library" refer to a plurality of molecules, which may be termed "members," synthesized or otherwise prepared from one or more starting materials by employing either the same or different reactants or reaction conditions at each reaction in the library. In general, the members of any library show at least some structural diversity, which often results in chemical and biological diversity. Such structural diversity in preparing libraries of coordination molecules may include, by way of example, metal ion diversity, ligand diversity, solvation diversity or counter-ion diversity. A library may contain any number of members from two different members to about $10^8$ members or more. In certain embodiments, libraries of the present invention have more than about 12, 50 and 90 members. In certain embodiments of the present invention, the starting materials and certain of the reactants are the same, and chemical diversity in such libraries is achieved by varying at least one of the reactants or reaction conditions during the preparation of the library. Combinatorial libraries of the present invention may be prepared in solution or on the solid phase. Further details regarding the libraries of the present invention are described below.

"Modulation" refers to up regulation (i.e., activation or stimulation), down regulation (i.e., inhibition or suppression) of a response, or the two in combination or apart.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

A "patient" or "subject" or "host" refers to either a human or non-human animal. The "non-human animals" of the invention comprise any non-human animal that is capable of expressing the subject genes and gene products. Such non-human animals include vertebrates such as rodents, non-human primates, ovines, bovines, ruminants, lagomorphs, porcines, caprines, equines, canines, felines, aves, piscines, etc. In certain embodiments of the invention, the animals are mammals. Exemplary non-human mammals are porcines (e.g., pigs), murines (e.g., rats, mice, and lagomorphs (e.g., rabbits)), and non-human primates (e.g. monkeys and apes).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The phrase "selective inhibitor of ATP production" refers to any compound that is able to specifically modulate the activity of hexokinase or another enzyme that is limiting in the rapid ATP production that provides for the rapid growth of a cancerous tumor. For example, such metabolic pathways include the glycolytic pathway, oxidative phosphorylation pathway, and mitochondrial respiration.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating red cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics.

"Therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a at a reasonable benefit/risk ratio applicable to such treatment.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented.

2. General

We have demonstrated herein that the VX2 tumor exhibits a high glycolytic/high hexokinase phenotype, and that a large fraction of the total cell hexokinase is mitochondrially bound. Therefore, the VX2 tumor model may be used in therapeutic screening for inhibitors of tumor metabolic activity, particularly ATP synthesis, that do not damage the surrounding liver tissue and are not toxic to the host. In addition, we describe herein the results of a screen for selective inhibitors of VX2 tumor ATP production that may be used in therapeutic methods for cancer.

We also describe a novel strategy that comprises direct intraarterial delivery to liver tumors of the compound 3-bromopyruvic acid (3-BrPA), a strong alkylating agent that abolishes cell ATP production via inhibition of both glycolysis and oxidative phosphorylation. The use of 3-BrPA as a putative therapeutic agent was first suggested by results we obtained using our VX2 tumor inhibitor screening methods. As described herein, we have now demonstrated using a rabbit model that this unique approach shows promise as a rapid effective therapy for liver cancer. We have shown that this strategy is highly effective, reducing in a single injection the total number of viable cells in liver implanted rabbit tumors to as low as 10% without doing any apparent harm to the animals or their major tissues.

As an unexpected extension of our original objective, we have shown also that systemic delivery of 3-BrPA to the same animals bearing the liver implanted tumors, also does no apparent harm to the animals or their major tissues, but suppresses secondary "metastatic" tumors that appear in the lungs. Thus, it is possible with a single, carefully selected known chemical agent, and a combination of intraarterial and systemic delivery methods, to inflict extensive damage on both a primary tumor and a secondary "metastatic" tumor within the same host without doing noticeable harm to the host.

3. Inhibitors of ATP Production

In another aspect, the invention provides selective inhibitors of ATP production represented in the general formula:

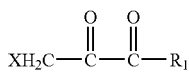

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain other embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate is selected from the group consisting of: triflate, mesylate and tosylate. In yet another embodiment, X is an amine oxide is dimethylamine oxide. In certain embodiments $R_1$ represents OR, H, N(R")$_2$, C1-C6 alkyl, C6-C12 aryl, C1-C6 heteroalkyl, or a C6-C12 heteroaryl. Independently, in other embodiments, R" represents H, C1-C6 alkyl, or C6-C12 aryl. Independently, in still other embodiments, R represents H, alkali metal, C1-C6 alkyl, C6-C12 aryl or C(O)R'; and R' represents H, C1-C20 alkyl or C6-C12 aryl.

In a preferred embodiment, the invention further provides inhibitors of ATP production represented in general formula:

X—CH2-CO—COOH, wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate is selected from the group consisting of: triflate, mesylate and tosylate. In yet another embodiment, X is an amine oxide is dimethylamine oxide.

4. Methods of Identifying Selective Inhibitors of ATP Production

In another aspect, the present invention provides, in part, methods for screening inhibitors of ATP production that may be used to treat a cancerous tumor. In one embodiment, the method for identifying a selective inhibitor of ATP production, comprises:

(a) contacting at least a portion of a VX2 tumor with a candidate inhibitor; and (b) assaying for ability of said candidate inhibitor to modulate the activity of a polypeptide comprising a pathway involved in ATP synthesis in said tumor, wherein the ability to modulate said activity indicates said candidate inhibitor may be a selective ATP synthesis inhibitor. In certain embodiments, the tumor is implanted in a host. In certain embodiments, the assaying step comprises assaying the ability of said candidate inhibitor to modulate the activity of an enzyme in the glycolytic pathway. For example, glycolysis may be assayed by monitoring the formation of lactic acid following the addition of glucose to a medium containing VX2 tumor slices. In one embodiment, the enzyme is a hexokinase. Preferred assays include but are not limited to those described in Examples 3 through 6 and 9 through 10. In other embodiments, the assaying step comprises assaying the ability of said candidate inhibitor to modulate the activity of an enzyme in the mitochondrial respiration pathway.

In another embodiment, a method for identifying a selective inhibitor of ATP production comprises:

(a) contacting a cell derived from a VX2 tumor with a candidate inhibitor; and;

(b) assaying for ability of said candidate inhibitor to modulate the activity of a polypeptide comprising a pathway involved in ATP synthesis in said cell, wherein the ability to modulate said activity indicates said candidate inhibitor may be a selective ATP synthesis inhibitor.

At least a portion of a VX2 tumor may be used in the above-described methods. Portions of a VX2 tumor may be derived, for example by slicing or microtoming an extracted VX2 tumor. In certain embodiments, a whole VX2 tumor is isolated from a host and used in a screen. In still other embodiments, the VX2 tumor is implanted in a host. Methods for isolating and implanting such tumors are known in the art, and examples of such may be found in the Exemplification herein.

In other embodiments, the method comprises the use of cell lines derived from a VX2 tumor. The VX2 tumor may be utilized both as sources of cells for in vitro culture by means of standard culturing techniques. Culturing techniques well-known in the art make it possible to obtain primary cultures which can be utilized directly as nontransformed lines for the screening of substances with inhibitory activity, or can be transformed in order to obtain lines whose cells continue to proliferate, e.g. in an immortalized cell line. These cultures can be used, for example, in the screening of compounds with a therapeutic effect on cancerous tumors, according the methods of the present invention. Such primary and immortalized cell cultures comprise the "cell lines" of the present invention. Such VX2 tumor cell lines may be prepared from any cell derived from a VX2 tumor.

The above-described cell lines may be cultured using well-known techniques of cell culture. Suitable media for culture include natural media based on tissue extracts and bodily fluids as well chemically defined media. Media suitable for use with the present invention include media containing serum as well as media that is serum-free. Serum may be from any source, including calf, fetal bovine, horse, and human serum. Any selected medium may contain one or more of the following in any suitable combination: basal media, water, buffers, free-radical scavengers, detergents, surfactants, polymers, cellulose, salts, amino acids, vitamins, carbon sources, organic supplements, hormones, growth factors, antibiotics, nutrients and metabolites, lipids, minerals, and inhibitors. Media may be selected or developed so that a particular pH, $CO_2$ tension, oxygen tension, osmolality, viscosity, and/or surface tension results from the composition of the medium. The incubation steps of the above method may be accomplished by maintaining the cell cultures in an environment wherein temperature and atmosphere are controlled. The culture conditions may be altered to maintain cellular proliferation and contractile activity in the cell cultures (optimum culture conditions are described below).

Assays and methods of developing assays appropriate for use in the methods described above are known to those of skill in the art, and are contemplated for use as appropriate with the methods of the present invention. In certain embodiments of the present invention, a candidate compound may be evaluated by an in vitro assay. In certain embodiments, the assay may be an in vivo assay. Assays may be conducted to identify molecules that modulate the activity of a protein, preferably an enzyme in a pathway involved in ATP production. Such assays are well-known to one of skill in the art and may be adapted to the methods of the present invention with no more than routine experimentation.

Candidate inhibitors may be selected from a library of such compounds. The synthesis and screening of combinatorial libraries is a validated strategy for the identification and study of compounds of interest. According to the present invention, the synthesis of libraries containing molecules or compounds may be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", *Chemical and Engineering News*, Feb. 24, 1997, p. 43; Thompson et al., *Chem. Rev.* (1996) 96:555). Many libraries are commercially available. One of ordinary skill in the art will realize that the choice of method for any particular embodiment will depend upon the specific number of molecules to be synthesized, the specific reaction chemistry, and the availability of specific instrumentation, such as robotic instrumentation for the preparation and analysis of the inventive libraries. In certain embodiments, the reactions to be performed to generate the libraries are selected for their ability to proceed in high yield, and in a stereoselective and regioselective fashion, if applicable.

All of the above screening methods may be accomplished using a variety of assay formats. In light of the present disclosure, those not expressly described herein will nevertheless be known and comprehended by one of ordinary skill in the art. The assays may identify compounds which are, e.g., either agonists or antagonists, of activity of a target protein of interest, or of a protein:protein or protein-substrate interaction of a target of interest, or of the role of target proteins in the pathogenesis of normal or abnormal cellular physiology, proliferation, and/or differentiation and disorders related thereto. The assays may further identify compounds which affect the generation of normal or abnormal cellular physiology, cell proliferation, and/or cell differentiation and disorders related thereto. Assay formats which approximate such conditions as formation of protein complexes or protein-nucleic acid complexes, enzymatic activity, and even specific signaling pathways in cardiac cells, may be generated in many different forms, and include but are not limited to assays based on cell-free systems, e.g. purified proteins or cell lysates, as well as cell-based assays which utilize intact cells or tissues such as at least a portion of a VX2 tumor.

The activity of a polypeptide of the invention may be identified and/or assayed using a variety of methods well known to the skilled artisan. For example, the activity of a protein may be assayed using an appropriate substrate or binding partner or other reagent suitable to test for the suspected activity. For catalytic activity, the assay is typically designed so that the enzymatic reaction produces a detectable signal. In one embodiment, a radioactive substrate may be used to detect the enzymatic reaction. For example, mixture of a kinase with a substrate in the presence of $^{32}P$ will result in incorporation of the $^{32}P$ into the substrate. The labeled substrate may then be separated from the free $^{32}P$ and the presence and/or amount of radiolabeled substrate may be detected using a scintillation counter or a phosphorimager. In another example, chromogenic or fluorogenic substrates may be used to detect the enzymatic reaction. For example, after protease hydrolysis of a peptidyl naphtylamide substrates, the liberated 2-naphtylamide is converted to a colored azo dye by coupling with a diazonium salt that can be measured using a spectrophotometer. In another example, the enzymatic activity may be coupled to another reaction, e.g. glucose-6-phosphate formed in a hexokinase reaction may be coupled to the glucose-6-phosphate dehydrogenase reaction. In this example NADP+ oxidizes glucose-6-phosphate to a g-lactone while becoming reduced to NADPH, thus allowing the formation of the latter to be monitored spectrophotometrically at 340 nm. Similar assays may be designed to identify and/or assay the activity of a wide variety of enzymatic activities. Based on the teachings herein, the skilled artisan would readily be able to develop an appropriate assay for a target enzyme.

5. Pharmaceutical Compositions of the Subject Inhibitors

The invention provides pharmaceutical compositions comprising the above-described inhibitor compounds In one aspect, the present invention provides pharmaceutically acceptable compositions which comprise a therapeutically-effective amount of one or more of the compounds described above, formulated together with one or more pharmaceutically acceptable carriers (additives) and/or diluents. In another aspect, certain embodiments, the compounds of the invention can be administered as such or in admixtures with pharmaceutically acceptable carriers and can also be administered in conjunction with other chemotherapeutic agents or scavenger compounds. Conjunctive therapy thus includes sequential, simultaneous and separate, or co-administration of the active compound in a way that the therapeutical effects of the first administered one is not entirely disappeared when the subsequent is administered.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

In a preferred embodiment, the pharmaceutical compositions are formulated for parenteral administration. In one embodiment, the pharmaceutical composition is formulated for intraarterial injection. In another preferred embodiment, the pharmaceutical compositions are formulated for systemic administration.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In certain embodiments, the above-described pharmaceutical compositions comprise one or more of the inhibitors, a second chemotherapeutic agent, and optionally a pharmaceutically acceptable carrier.

The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following additional drugs may also be used in combination with the antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and pro-drugs.

Preferred chemotherapeutic agents for use with the compositions and methods of treatment described herein include, but are not limited to altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

In another preferred embodiment, the composition of the invention may comprise other biologically active substances, preferably a therapeutic drug or pro-drug, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically activated when implanted, injected or otherwise inserted into the tumor.

6. Therapeutic Methods

The present invention further provides novel therapeutic methods of treating a cancerous tumor comprising administering to the subject an effective amount of a subject pharmaceutical composition. The methods of the present invention may be used to treat any cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow or uterine tissue.

In certain embodiments, the method comprises parenterally administering an effective amount of a subject pharmaceutical composition to a subject. In one embodiment, the method comprises intraarterial administration of a subject composition to a subject. In other embodiments, the method comprises administering an effective amount of a subject composition directly to the arterial blood supply of a cancerous tumor in a subject. In one embodiment, the methods comprises administering an effective amount of a subject composition directly to the arterial blood supply of the cancerous tumor using a catheter. In embodiments where a catheter is used to administer a subject composition, the insertion of the catheter may be guided or observed by fluoroscopy or other method known in the art by which catheter insertion may be observed and/or guided. In another embodiment, the method comprises chemoembolization. For example a chemoembolization method may comprise blocking a vessel feeding the cancerous tumor with a composition comprised of a resin-like material mixed with an oil base (e.g., polyvinyl alcohol in Ethiodol) and one or more chemotherapeutic agents. In still other embodiments, the method comprises systemic administration of a subject composition to a subject.

In certain embodiments, the methods of treating a cancerous tumor comprise administering one or more selective inhibitors of the invention in conjunction with a second agent to a subject. Such methods in certain embodiments comprise administering pharmaceutical compositions comprising one or more inhibitors in conjunction with other chemotherapeutic agents or scavenger compounds. Conjunctive therapy includes sequential, simultaneous and separate, or co-administration of the active compound in a way that the therapeutical effects of the first administered one is not entirely disappeared when the subsequent is administered. In one embodiment, the second agent is a chemotherapeutic agent. In another embodiment, the second agent is a scavenger compound. In certain embodiments, the second agent may be formulated into a separate pharmaceutical composition. In other embodiments, the pharmaceutical composition may comprise both an inhibitor and a second agent.

In other embodiments, the methods of treating a cancerous tumor comprise administering an effective amount of a subject composition directly to the blood vessels in the liver, head, neck, glands, or bones. For example, blood vessels such as the hepatic, femoral, cerebral, carotid, or vertebral arteries may be infused, injected, chemoembolized, or catheterized to administer the subject compositions to a cancerous tumor. In other embodiments, the methods comprise administering an effective amount of a subject composition directly to the blood vessels in a cancerous tumor in the head, neck, or bones. Such methods are well-known and used in the art. For example, Gobin, Y. P, et al (2001) Radiology 218:724-732 teaches a method for interarterial chemotherapy for brain tumors. Moser, et al. (2002) Head Neck 24:566-74 reviews the use of intraarterial catheters for chemotherapeutic treatment in head and neck cancer. Wang, M. Q., et al. (2001) J. Vasc. Interv. Radiol. 12:731-7 teaches a method of injecting the femoral arteries as well as a method of chemoembolization in order to treat osteosarcoma. Kato, T., et al. (1996) Cancer Chemother Pharmacol 37(4):289-96 reviews the use of intraarterial infusion of microencapsulated anticancer drugs (chemoembolization) to treat cancerous tumors in the liver, kidney, intrapelvic organs, lung, head and neck, and bones. Hermann, K., et al (2000) Radiology 215:294-9; Kemeny, N. E., (1999) Baillieres Best Pract Res Clin Gastroenterol 13:593-610 describe exemplary methods of intraarterial and embolization methods for treatment of liver cancer.

In general, chemoembolization or direct intraarterial or intravenous injection therapy utilizing pharmaceutical compositions of the present invention is typically performed in a similar manner, regardless of the site. Briefly, angiography (a road map of the blood vessels), or more specifically in certain embodiments, arteriography, of the area to be embolized may be first performed by injecting radiopaque contrast through a catheter inserted into an artery or vein (depending on the site to be embolized or injected) as an X-ray is taken. The catheter may be inserted either percutaneously or by surgery. The blood vessel may be then embolized by refluxing pharmaceutical compositions of the present invention through the catheter, until flow is observed to cease. Occlusion may be confirmed by repeating the angiogram. In embodiments where direct injection is used, the blood vessel is then infused with a pharmaceutical composition of the invention in the desired dose.

Embolization therapy generally results in the distribution of compositions containing inhibitors throughout the interstices of the tumor or vascular mass to be treated. The physical bulk of the embolic particles clogging the arterial lumen results in the occlusion of the blood supply. In addition to this effect, the presence of an anti-angiogenic factor(s) prevents the formation of new blood vessels to supply the tumor or vascular mass, enhancing the devitalizing effect of cutting off the blood supply. Direct intraarterial or intravenous generally results in distribution of compositions containing inhibitors throughout the interstices of the tumor or vascular mass to be treated as well. However, the blood supply is not generally expected to become occluded with this method.

Within one aspect of the present invention, primary and secondary tumors of the liver or other tissues may be treated utilizing embolization or direct intraarterial or intravenous injection therapy. Briefly, a catheter is inserted via the femoral or brachial artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting compositions (as described above) through the arterial catheter until flow in the artery to be blocked ceases, preferably even after observation for 5 minutes. Occlusion of the artery may be confirmed by injecting radio-opaque contrast through the catheter and demonstrating by fluoroscopy or X-ray film that the vessel which previously filled with contrast no longer does so. In embodiments where direct injection is used, the artery is infused by injecting compositions (as described above) through the arterial catheter in a desired dose. The same procedure may be repeated with each feeding artery to be occluded.

For use in embolization therapy, compositions of the present invention are preferably non-toxic, thrombogenic, easy to inject down vascular catheters, radio-opaque, rapid and permanent in effect, sterile, and readily available in different shapes or sizes at the time of the procedure. In addition, the compositions preferably result in the slow (ideally, over a period of several weeks to months) release of an inhibitor and/or a second agent. Particularly preferred compositions should have a predictable size of 15-200 .microns after being injected into the vascular system. Preferably, they should not clump into larger particles either in solution or once injected. In addition, preferable compositions should not change shape or physical properties In most embodiments, the subject pharmaceutical compositions will incorporate the substance or substances to be delivered in an amount sufficient to deliver to a patient a therapeutically effective amount of an incorporated therapeutic agent or other material as part of a prophylactic or therapeutic treatment. The desired concentration of active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

For the subject compositions, a range of dosage is contemplated by the present invention. The present invention contemplates embodiments that release at least those amounts over a three week period, at least twice those amounts over a six week period, etc.

Dosage may be based on the amount of the composition per kg body weight of the patient. For example, a range of amounts of compositions are contemplated, including about 0.001, 0.01, 0.1, 0.5, 1, 10, 15, 20, 25, 50 mg or more of such compositions per kg body weight of the patient. Other amounts will be known to those of skill in the art and readily determined.

In certain embodiments, the dosage of the subject compounds will generally be in the range of about 0.001 mg to about 10 mg per kg body weight, specifically in the range of about 0.1 mg to about 10 mg per kg, and more specifically in the range of about 0.1 mg to about 1 mg per kg. In one embodiment, the dosage is in the range of about 0.3 mg to about 0.6 mg per kg. In one embodiment, the dosage is in the range of about 0.4 mg to about 0.5 mg per kg.

Alternatively, the dosage of the subject invention may be determined by reference to the plasma concentrations of the composition. For example, the maximum plasma concentration (Cmax) and the area under the plasma concentration-tiem curve from time 0 to infinity (AUC (0-4)) may be used. Dosages for the present invention include those that produce the above values for Cmax and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

7. Kits

The present invention provides kits for treating various cancers. For example, a kit may comprise one or more pharmaceutical compositions as described above. The compositions may be pharmaceutical compositions comprising a pharmaceutically acceptable excipient. In other embodiments involving kits, this invention provides a kit including pharmaceutical compositions of the present invention, and optionally instructions for their use. In still other embodiments, the invention provides a kits comprising one more more pharmaceutical compositions and one or more devices for accomplishing administration of such compositions. For example, a subject kit may comprise a pharmaceutical composition and catheter for accomplishing direct intraarterial injection of the composition into a cancerous tumor. In one embodiment, the device is an intraarterial catheter. Such kits may have a variety of uses, including, for example, therapy, diagnosis, and other applications.

EXEMPLIFICATION

The invention now being generally described, it will be more readily understood by reference to the following examples which are included merely for purposes of illustration of certain aspects and embodiments of the present invention, and are not intended to limit the invention in any way.

Examples 1 through 11 describe work done with VX2 tumors to characterize the energy metabolism of the VX2 tumor, and to screen inhibitors of the metabolism in the VX2 tumor. Example 12 through 20 describe work done with VX2 tumors implanted in a rabbit host, including the administration of the inhibitors identified in Examples 10 and 11 to the host in order to study the effect of the inhibitors in treating the tumor.

VX2 Tumor Studies and Inhibitor Screens

Example 1

Materials for VX2 Tumor Experiments

New Zealand white rabbits weighing 3.5-4.2 kg were obtained from Robinson Services Inc. The VX2 tumor, normally grown in the hind limb of these animals, was obtained locally from Dr. John Hilton, Department of Oncology, Johns Hopkins University School of Medicine. AS-30D hepatoma cells, an established line, is maintained by Min Gyu Lee in the inventors' laboratory. This is done by growth and passage of the cells in the peritoneal cavity of female Sprague Dawley rats (Charles River Breeding Laboratories). The following agents were obtained from Sigma: D-glucose, 2-deoxyglucose, 2-fluoro-2-deoxyglucose, 6-fluoro-6-deoxyglucose, 3-O-methylglucose, 5-thio-D-glucose-6-phosphate, L-glucose, D-xylose, D-lyxose, 3-bromopyruvic acid, ATP, ADP, NADP+, D-mannitol, Hepes, succinate, oligomycin, and bovine albumin. The lactic acid kit containing lactic dehydrogenase, NAD+, hydrazine, and a glycine buffer, pH 9.2 was obtained also from Sigma. NaPi, KPi, and sucrose were obtained from J. T. Baker, and the Coomassie dye binding agent from Pierce. Glucose-6-phosphate dehydrogenase was obtained from Roche Molecular Biochemicals, and both the DMEM tissue culture medium and trypan blue were from Life Technologies Gibco BRL. The Clark oxygen electrode was purchased from Yellow Springs Instruments.

Example 2

Processing the VX2 Tumor for Biochemical Analyses

In one set of studies the VX2 tumors, which had grown in the hind limb of New Zealand white rabbits for 4 weeks, were excised, cut into 1 g pieces (ca. 10 mm×10 mm×10 mm) with a razor blade, and then subjected to assays described below for monitoring both glycolytic and hexokinase activities. In a second set of studies VX2 tumors, which had grown in the hind limb of a New Zealand white rabbit for about 2 weeks, were excised, broken into small chunks (<0.1 g), and then implanted into the livers of a number of other rabbits. Following implantation, VX2 tumors rapidly developed in the livers of each animal. They were excised at different times ranging from 2 to 5.7 weeks and also subjected to the assays described below for monitoring glycolytic and hexokinase activities, as well as an assay for monitoring mitochondrial respiration. In all cases the exterior surface of the tumor was shaved to remove any remaining normal tissue. In addition, special care was taken to assure that only the viable portion of the tumor located near or on the surface was removed for analyses. The preparation of the animals for surgery, and the surgical and implantation procedures, have been described. These procedures were approved by the Animal Care and Use Committee at the Johns Hopkins University School of Medicine and conducted according to their guidelines.

Example 3

Assay for Glycolytic Activity in the VX2 Tumor

Glycolysis was assayed by monitoring the formation of lactic acid following the addition of glucose to a medium containing VX2 tumor slices. Specifically, freshly excised tumors were washed 3 times at 4° C. in 20 ml Chance Hess Medium containing 6.2 mM KCl, 154 mM NaCl, and 11 mM NaPi, pH 7.4. Slices, 1 g each, were then prior incubated for 30 min in a Lab-Line incubator-shaker at 37° C. in 2 ml of the same medium while shaking at 50 rpm. Glucose was then added to give a final concentration of 6 mM, after which the incubation/shaking process was continued with 0.2 ml samples being removed every 30 min for up to 2 h. Then, samples were removed for analysis at 2 additional time points indicated in the Figure. These samples were subjected to centrifugation at 14,000 rpm in an Eppendorf Centrifuge (Model 5415C). Then, aliquots of the supernatant, 0.01 ml, were removed from each sample, diluted with 0.03 ml of water and subjected to lactic acid determination using the kit supplied by Sigma. The latter contains, in addition to lactic dehydrogenase and NAD+, hydrazine, and glycine buffer, pH 9.2. The mixture was incubated for 30 min at 25° C. after which the absorbance due to formation of NADH was determined at 340 nm using a Gilford Model 260 spectrophotometer. To assess the elevation of the glycolytic activity of the VX2 tumor over that of liver tissue, parallel studies were always carried out in an identical manner with 1 g liver slices derived from the host liver. Finally, in those cases where agents were tested for their capacity to inhibit glycolysis, these were introduced into the system at the prior incubation step with all subsequent steps being run in parallel with those described above for the VX2 tumor or liver alone.

Example 4

Preparation of Subcellular Fractions for Hexokinase and Mitochondrial Respiration Assays The freshly isolated liver or VX2 tumor tissues (15-20 g wet weight) was rinsed in 3 volumes of H-medium (210 mM D-mannitol, 70 mM sucrose, 2 mM Hepes, and 0.05% bovine albumin, pH 7.4) at 4° C. and minced with a razor blade as finely as possible. A 30% (V/V) suspension was made using ice-cold H-medium in a Potter-Elvehjem glass homogenizer (55 ml capacity), and homogenization was achieved by applying 4 complete up and down strokes through the suspension with a rotating (~400 rpm), serrated, teflon pestle attached to a motor. To remove cell debris and nuclei, the resultant homogenate was diluted to twice the initial volume and centrifuged at 630×g for 8 minutes at 4° C. in a Sorvall RC-2B centrifuge using a GSA rotor. The supernatant was removed and then centrifuged at 6,800 g for 15 min under the same conditions. The resultant supernatant was saved and referred to here as the cytosolic faction. The pellet was resuspended in the initial volume of H-medium and centrifuged twice at 9,800×g for 15 min at 4° C. The washed pellet represents the mitochondrial fraction.

Example 5

Assay for Hexokinase Activity

The assay coupled the glucose-6-phosphate formed in the hexokinase reaction to the glucose-6-phosphate dehydrogenase reaction. Here, NADP+, oxidizes glucose-6-phosphate to a g-lactone while becoming reduced to NADPH, thus allowing the formation of the latter to be monitored spectrophotometrically at 340 nm. The final reaction mixture contained the following ingredients in a total volume of 1 ml at 25° C.: 25 mM triethanolamine, pH 7.6, 15 mM MgCl2, 1 mM dithiothreitol, 0.45 mM NaCN, 0.005 mg/ml oligomycin, 0.014 mM DAPP [P1,P5-Di(adenosine-5')pentaphosphate], 5 mM ATP, 3.3 units glucose-6-phosphate dehydrogenase, 1 mM NADP+, 0.1-0.3 mg cytosolic or mitochondrial fraction, and concentrations of glucose as indicated in the figure legends. Glucose was used to initiate the reaction.

Example 6

Assay for Mitochondrial Respiration

Oxygen consumption rates were measured polarographically using a Clark oxygen electrode inserted into a 2.5 ml chamber equipped with a magnetic stirrer. The electrode was connected to a chart recorder calibrated between 0 and 100% saturation with atmospheric oxygen at 25° C. The loss of oxygen was monitored in a 2.1 ml system at 25° C. containing 1 mg mitochondria, 0.5 mM EDTA, 2.0 mM Hepes, 220 mM D-mannitol, 70 mM sucrose, 2.5 mM KPi, 2.6 mM MgCl2, and 0.5 mg/ml bovine albumin, and, where indicated, 7.8 mM succinate (respiratory substrate), and 0.24 mM ADP (ATP synthesis substrate).

Example 7

AS-30D Hepatoma Cells: Culture Conditions, and Assessment of Cell Viability

AS-30D hepatoma cells grown in the peritoneal cavity of Sprague Dawley female rats (see Materials) were adapted to grow in tissue culture in Dulbecco's modified Eagle's medium containing 10% fetal bovine serum. Cells were maintained at 37° C. in a humidified atmosphere containing 5% CO2, and counted in a Neubauer chamber after trypan blue dye addition (cell/dye volume=1/1) by visualization under a Nikon inverted microscope.

Example 8

Description of the VX2 Tumor Prior to and After Liver Implantation

Photographs of VX2 tumors representative of those used in this study are presented in FIG. 1. When excised from the hind limb of the New Zealand white rabbit (donor) at 4 weeks the tumor is about 10 g in weight, flesh colored with some surface vascularization, and without any obvious signs of necrosis (FIG. 1A). When small chunks (<0.1 g) are implanted in the liver of a rabbit of similar size and age the tumor grows rapidly attaining a weight as high as 25 g in a 4 week period while retaining its solid, flesh colored features (FIG. 1C). Here too, there are no obvious signs of necrosis although an increased surface vascularization is apparent. At 5.7 weeks (FIG. 1D), the liver implanted VX2 tumor has become highly vascularized on its surface and more than doubled in size in the intervening 1.7 weeks. Much of the increased weight is due to fluid that has accumulated within the core of the tumor where it has become almost completely necrotic and taken on a mush-like texture. At this stage only the tissue near the surface of the tumor remains viable and can be used for biochemical studies. Tumors were not carried beyond 5.7 weeks.

Example 9

Figure 2:
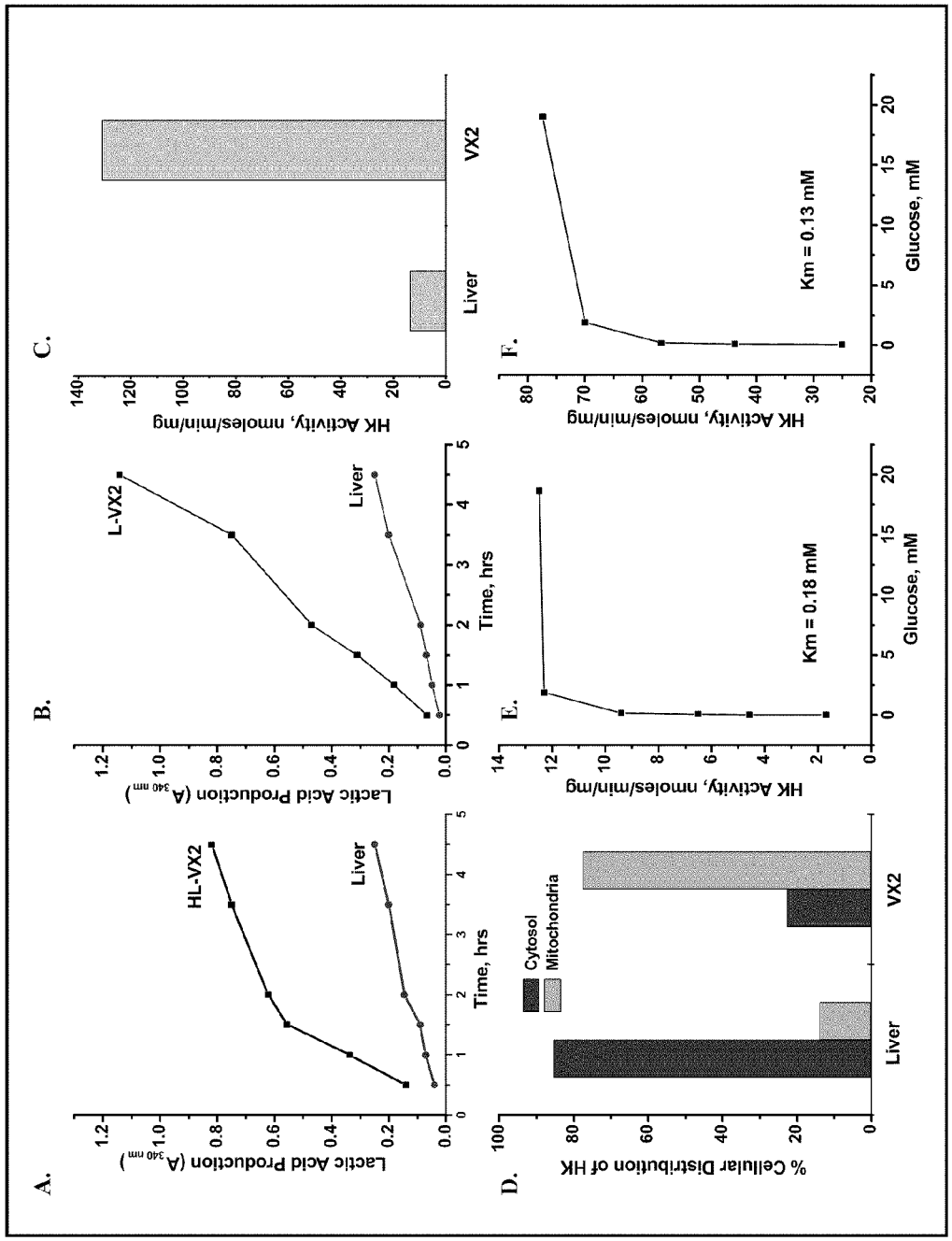
FIGS. 2A and B depict lactic acid production by the VX2 tumors isolated, respectively, from the rabbit hind limb (HL-VX2) and rabbit liver (L-VX2). In both cases, slices of the tumors were incubated in the presence of 6 mM glucose for the times indicated and then assayed for lactic acid as described in the Exemplification. Liver slices from the animals from which the tumors were obtained were subjected to the same assay.
FIG. 2C depicts a comparison of the activity of hexokinase per mg protein in liver and VX2 tumor tissues. The mean±standard error are 13.7±2.5 (liver) and 131±10.1 (tumor). Details of the assay are described in the Exemplification.
FIG. 2D depicts the relative distribution of total hexokinase activity in the mitochondrial and cytosolic fractions of rabbit liver and VX2 tumor tissues. For liver, the mean±standard error in % of total cellular distribution is 85.3±2.6 (cytosol) and 13.7±2.5 (mitochondria). For the VX2 tumor these values are 22.6±6 (cytosol) and 77.4±6 (mitochondria). The % of the total starting protein recovered in the mitochondrial fraction (~20-21%) was nearly the same for liver and tumor.
FIGS. 2E and 2F depict Michaelis-Menten kinetic constants (Km values for glucose) for hexokinase located, respectively, in the cytosolic and mitochondrial fractions of the VX2 tumor. The mean±standard error is 0.18±0.015 mM (cytosolic fraction) and 0.13±0.02 mM (mitochondrial fraction).

Glycolytic Capacity and Hexokinase Activity of the VX2 Tumor Prior to and After Liver Implantation Results of experiments presented in FIG. 2A show that slices of the VX2 tumor isolated after 4 weeks of growth in the hind limb of a New Zealand white rabbit exhibit a glycolytic rate that is 7.4 fold higher than that observed for normal liver tissue derived from the same animal. Significantly, this enhanced glycolytic rate of the VX2 tumor relative to liver tissue is retained when small chunks of the tumor (<0.1 g) are implanted in the liver of another rabbit of similar size and age. Thus, FIG. 2B shows that the glycolytic rate of tumor slices derived from the liver implanted VX2 tumor after 4 weeks of growth is 8.3 fold higher than the glycolytic rate obtained with liver slices obtained from the same liver in which the tumor implant had been made. This high glycolytic rate of the liver implanted VX2 tumor remained relatively constant through 5.7 weeks of growth.

Results presented in FIG. 2C show that the hexokinase activity is also markedly elevated (~9.5 fold) in the liver implanted VX2 tumor relative to the activity of this enzyme in the surrounding liver tissue. In addition, as shown in FIG. 2D, the subcellular distribution of this activity in the tumor (~70% in the mitochondrial fraction and ~30% in the cytosol) differs markedly from that in the surrounding liver tissue (~20% in the mitochondrial fraction and 80% in the cytosol). Finally, FIGS. 2E and 2F show that the Km of the tumor hexokinase(s) for glucose is very low (0.11 mM, mitochondrial fraction and 0.19 mM, cytosolic fraction, mean value of 3 experiments) reflecting a high apparent affinity of the isoform(s) for glucose. This is in sharp contrast to liver where the Km for glucose of the major hexokinase isoform involved, i.e., glucokinase, is at least 5 mM in most reported studies.

These studies show clearly that the VX2 tumor, although of non-hepatic origin, exhibits glucose metabolic properties characteristic of many rapidly growing hepatomas, the biochemical hallmarks of which are a high glycolytic/high hexokinase phenotype, and binding of the hexokinase (low Km for glucose) to the mitochondrial fraction.

Example 10

Screening of Inhibitors of the Glycolytic Capacity of the Isolated Liver Implanted VX2 Tumor A limited screen was carried out to identify inhibitors of the glycolytic capacity of the VX2 tumor with the purpose of selecting agents that might prove effective in arresting tumor cell growth. The screen included the following 9 compounds: 2-deoxyglucose (2DOG), 2-fluoro-2-deoxyglucose, 6-fluoro-6-deoxyglucose, 3-O-methyl glucose, 5-thio-D-glucose-6-phosphate, L-glucose, D-xylose, D-lyxose, and 3-bromopyruvic acid (3BrPA). The screen was conducted by incubating VX2 tumor slices in a medium containing 6 mM glucose with 6 mM of each of these agents at 37° C. for 5 h. The use of 6 mM glucose in the medium was used to mimic the maximal amount of glucose that might be in the blood in a real in vivo situation. All glucose analogs or other sugars tested under these conditions proved to be ineffective as inhibitors of VX2 tumor glycolysis indicating the inability of these sugars to act as effective glycolytic inhibitors under the conditions specified. In sharp contrast, the pyruvate analog (3BrPA) almost completely inhibited glycolysis.

Figure 3:
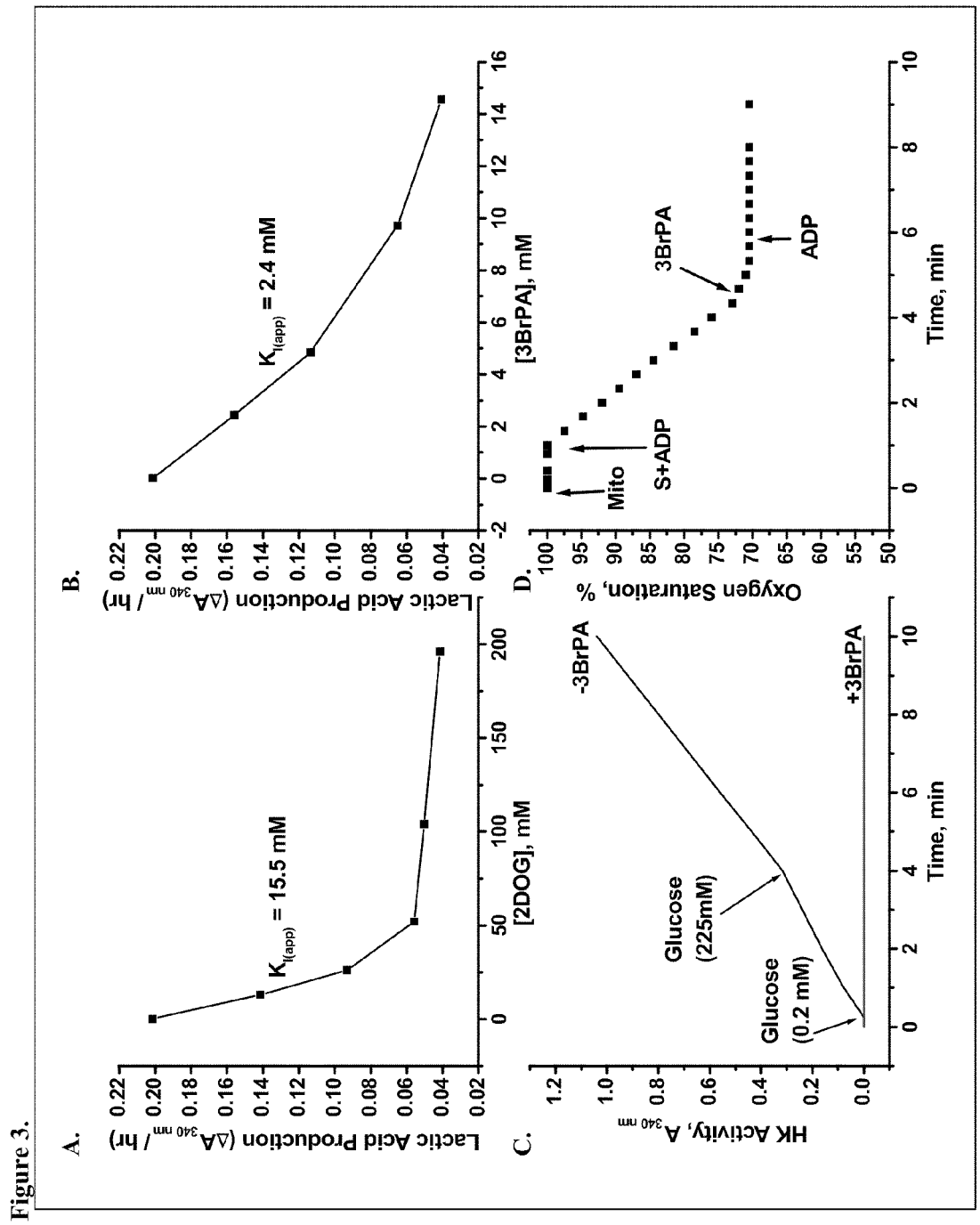
FIGS. 3A and 3B depict a comparison of the inhibitory effects, respectively, of 2DOG and 3BrPA on the glycolytic capacity of the isolated liver implanted VX2 tumor. In both cases various concentrations of 2DOG and 3BrPA were prior incubated for 30 min at 37° C. with 1 g VX2 tumor slices. Glycolysis was monitored as described in the Exemplification.
FIG. 3C depicts the effect of 3BrPA on the activity of hexokinase bound to the mitochondrial fraction of the VX2 tumor. Hexokinase activity was monitored as described in the Exemplification in the presence and absence of 5 mM 3BrPA.
FIG. 3D depicts the effect of 3BrPA on the ADP stimulated respiratory rate of rabbit VX2 tumor mitochondria. The procedures for preparing the mitochondria and assaying respiration are described in the Exemplification. Where indicated, 3BrPA was added to a final concentration of 1.2 mM.

With the above preliminary data at hand, only two of the 9 compounds screened were studied in more detail. One was 2DOG because under certain conditions it is known to inhibit glycolysis when it is phosphorylated by hexokinase to 2DOG-6-P which cannot be further metabolized. The other compound tested in more detail was 3BrPA because of its effectiveness as a glycolytic inhibitor in the preliminary screen. Data presented in FIG. 3A show that 2DOG can inhibit glycolysis catalyzed by VX2 tumor slices provided it is used at concentrations of glucose much higher than those normally found in the blood, and provided it is prior incubated with the tumor slices in the absence of glucose. Here, it can be seen that half maximal inhibition of glycolysis requires about 15 mM 2DOG whereas maximal inhibition (70%) requires almost 50 mM. Results presented in FIG. 3B show that 3BrPA is a more effective inhibitor than 2DOG as it induces half maximal inhibition of the glycolytic activity of the VX2 tumor slices at a concentration of only 2.4 mM and complete inhibition at about 15 mM.

Additional experiments were undertaken to determine whether 3BrPA is also an inhibitor of the mitochondrial hexokinase of the VX2 tumor, as this enzyme is known to be markedly elevated in rapidly growing hepatomas, and where examined carefully, to be required for maintenance of the high glycolytic rate. Results presented in FIG. 3C show that 5 mM 3BrPA inhibits completely glucose initiation of the hexokinase reaction in a system containing among other ingredients VX2 tumor mitochondria, ATP, glucose-6-phosphate dehydrogenase, and NADP+. Although complete inhibition of hexokinase activity is achieved at a concentration of only 5 mM 3BrPA (FIG. 3C), whereas a concentration near 15 mM is necessary to completely inhibit glycolysis (FIG. 3B), this is likely due to the fact that the former assay was conducted on a cell free extract whereas the latter was conducted on intact tumor tissue. Finally, in addition to these findings, was the very important discovery that 3BrPA (1.2 mM) also completely inhibits mitochondrial respiration (FIG. 3D), i.e., both the basal rate of respiration catalyzed by the respiratory substrate succinate, and the ADP stimulated rate of respiration normally associated with ATP synthesis by oxidative phosphorylation.

Example 11

Figure 4:
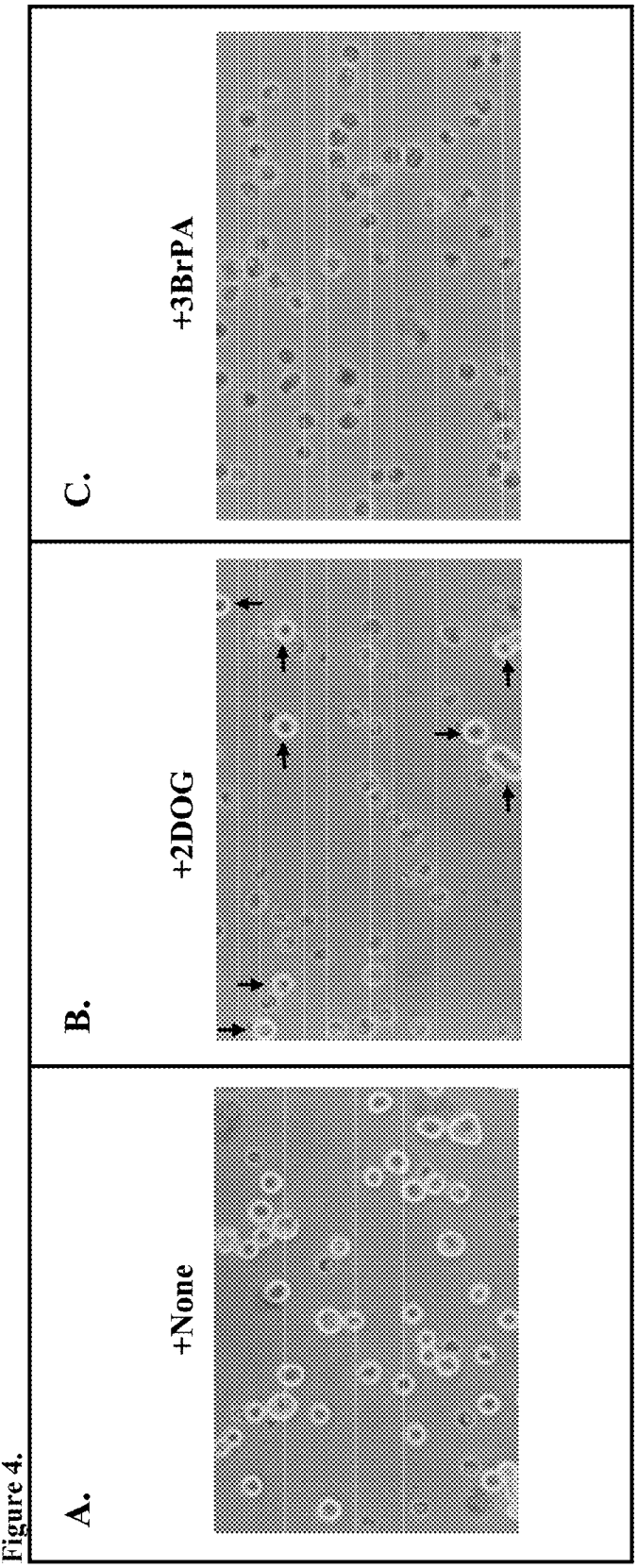
FIG. 4 depicts a comparison of the effects of 2DOG and 3BrPA on the viability of rat hepatoma cells growing in tissue culture. Cells were maintained in tissue culture as described in the Exemplification.

Comparison of the Relative Capacities of 2DOG and 3BrPA to Kill Hepatoma Cells Expressing the High Glycolytic/High Hexokinase Phenotype The studies described above using the VX2 tumor model for liver cancer predict that 2DOG and 3BrPA may have the capacity to kill hepatoma cells expressing the high glycolytic/high hexokinase phenotype. For this reason, both agents were tested for their capacity to inhibit the growth of AS-30D hepatoma cells, an established rat cell line known to exhibit a high glycolytic rate and to contain elevated levels of mitochondrial bound hexokinase. Significantly, comparison of control hepatoma cells (FIG. 4A) with those treated 12 h with 20 mM 2DOG (FIG. 4B) or with 5 mM 3BrPA (FIG. 4C) show that both 2DOG and 3BrPA have the capacity to induce cell death, with 3BrPA killing all cells in the population and 2DOG killing about 80%. Cell killing was assessed in these experiments by counting those cells in which trypan blue had entered.

In vivo Implanted VX2 Tumor Studies and Methods of Treatment Using Candidate Inhibitors Example 12

VX2 Tumor Iimplantation

The rabbit VX2 tumor was selected for implantation in the liver because of the similarities of its blood supply to that of human hepatomas. Other attributes of this tumor include rapid tumor growth, development of a sizable tumor that can be readily identified by x-ray imaging (fluoroscopy), and a biochemical phenotype characteristic of advanced stage tumors, i.e., high glycolysis and elevated levels of mitochondrial bound hexokinase. In addition, the rabbit is large enough that selective manipulation of catheters in the hepatic artery from the common femoral artery for delivery of agents is possible. Adult New Zealand white rabbits (32 total, Robinson Services, Inc.) weighing 3.5-4.2 kg were used. Studies with these animals were approved by the Johns Hopkins University Animal Care and Use Committee and carried out according to their guidelines. For successful implantation of the VX2 tumor into the liver, it was first grown for 2 weeks on the hind leg of a carrier rabbit. Each carrier rabbit was used to supply tumor cells for implantation into the left lobe of the liver of 2 separate rabbits. All animals, carriers and recipients, were anesthetized with a mixture of acepromazine (2.5 mg/kg) and ketamine hydrochloride (44 mg/kg) administered intramuscularly. Intravenous access was gained via a marginal ear vein and sodium pentothal was given intravenously to maintain anesthesia. The VX2 tumor was then excised from the carrier rabbit and placed in Hanks solution. Chunks of the tumor were minced in the same solution. Then, the abdomens of the recipient rabbits were shaved and prepped with betadine after which a midline subxyphoid incision was made. The anterior surface of the liver was exposed and tumor cells (0.1-0.2 ml) from the minced donor tumor were directly implanted onto the left lobe of the liver using the outer cannula of a 21-gauge angiocatheter. This method allows the growth of a single solitary, well-demarcated tumor in the liver of each recipient rabbit. The abdomen was closed in 2 layers. Proper aseptic technique was rigorously observed during each implantation. After surgery, animals were returned to their cages, kept warm with blankets, and monitored in the animal laboratory under the direct supervision of a physician or a technician until they recovered from anesthesia. Buprenorphine (0.01 mg) was administered for analgesia when the animals were in pain or showed physical distress. The tumors were allowed to grow for another 14 days at which time they reached an ellipsoidal shape with dimension of approximately 1.5×1.8×2.5 cm.

Example 13

Preparation of 3-BrPA Solutions

The solutions of 3-bromopyruvate (3-BrPA, Sigma Chemical Co., St. Louis, Mo.) were prepared in phosphate-buffered saline (PBS). After adjusting the pH to 7.0 with NaOH the solutions were sterilized via Millipore's Millexâ GV 0.22 mm filter unit and used immediately. Freshly made solutions were used in all studies reported here.

Example 14

Intraarterial Injection of 3-bromopyruvate (3-BrPyr)

Administration of anesthesia, intravenous access and sodium pentothal anesthesia were carried out as described in Example 12. Transcatheter hepatic artery injection of 3-BrPA was performed under fluoroscopy. The animals were brought to the angiography suite and intubated using a size 3.0 mm endotracheal tube (Mallinkrodt Medical, St. Louis, Mo.) but not ventilated. Surgical cut-down was performed to gain access into the right common femoral artery, after which a 3 French sheath (Cook Inc., Bloomington, Ind.) was placed. A specially manufactured 2 French catheter with a tip in the shape of a hockey-stick (JB1 catheter, Cook Inc., Bloomington, Ind.) was manipulated into the celiac axis after which a celiac arteriogram was performed in order to delineate the blood supply to the liver and confirm the location of the tumor. The tumor could readily be visualized as a region of hypervascular blush located on the left side of the liver near the gastric fundus. The left hepatic artery, which usually provides most of the blood flow to the tumor, was selectively catheterized via the common hepatic artery. When necessary, a steerable guidewire (0.010-0.014 inches Transend wire, Boston Scientific MediTech, Natick, Mass.) was used to help select the left hepatic artery. After having adequately positioned the catheter within the left hepatic artery, the 3-BrPA solution was infused directly into the artery. The animals were monitored after the procedure and given analgesics when they showed signs of physical distress.

Example 15

Embolization

This procedure was performed in a manner similar to the technique described above for 3-BrPA. However, instead of using 3-BrPA, a mixture of Ethiodol and embolic material (polyvinyl alcohol, Target Incorporated, Fremont, Calif.) was injected into the left hepatic artery. The procedure was considered successful when forward flow was no longer demonstrated within the left hepatic artery. In addition, an intense tumor stain was identified in each case suggesting a successful embolization procedure.

Example 16

Histopathology and Statistical Analysis

Normal tissues and tumors were fixed in 10% formalin, sliced at 5 mM intervals for gross examination, and then embedded completely in paraffin after which 4 m sections were stained with hemotoxylin and eosin. Tumor viability was estimated by visual inspection and expressed as a percentage of viable tumor area for each slice. The overall percentage of viable tumor in each rabbit was calculated.

The mean fractions of tumor necrosis+SD were compared using the unpaired Student t test for between group comparisons. Differences were considered statistically significant for $p<0.05$.

Example 17

Figure 5:
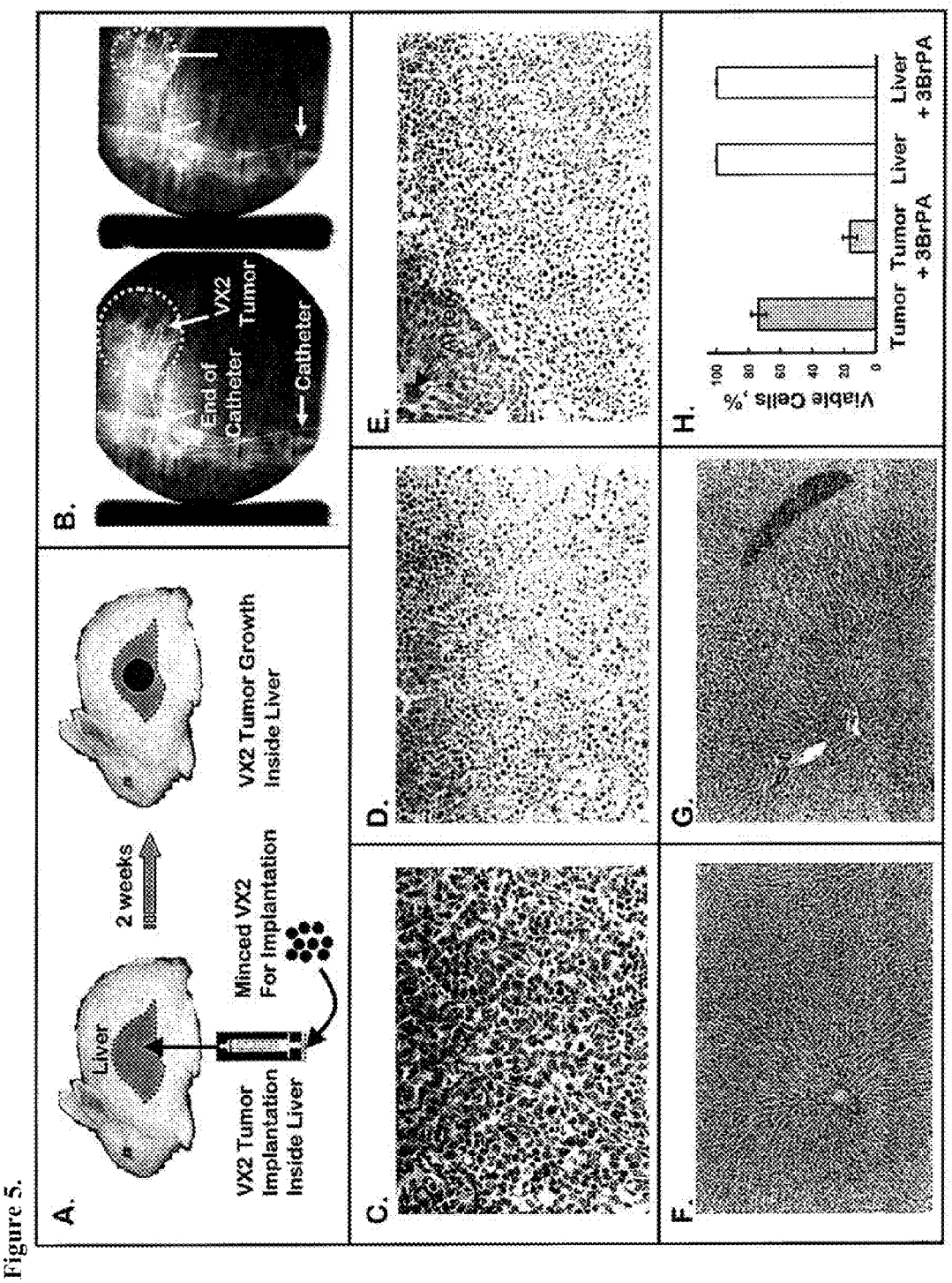
FIG. 5 depicts the experimental setup and effect of intraarterial injection of 3-BrPA on liver tumors.

Direct Intraarterial Injection of 3-BrPA into Liver Implanted VX2 Tumors Selectively Inhibits the Viability of Cells Therein without Altering the Viability of Surrounding Liver Tissue To test our hypothesis that direct intraarterial injection of a potent inhibitor of cell ATP production (3-BrPA) may selectively inhibit the viability of cells within the tumor, we employed the established VX2 tumor model for reasons described above. Small chunks of a donor VX2 tumor were minced, surgically implanted in the livers of 6 rabbits/experiment, and allowed to grow for 14 days (FIG. 5A). At this time, the single well-delineated tumor that developed in each liver exhibited a high degree of arterial vascularization due to the onset of angiogenesis. After fasting the animals for 24 hours and administering anesthesia, a catheter was carefully inserted into the femoral artery and guided by fluoroscopy into the hepatic artery to a position near the tumor site (FIG. 5B). Then, a single bolus injection of 3-BrPA was delivered in about 2 min directly into the artery. Animals treated identically, but not receiving 3-BrPA served as controls. Optimal results were obtained by delivering 25 ml 0.5 mM 3-BrPA, waiting 4 days, and then excising and subjecting each tumor, and the surrounding liver tissue, to histological analysis.

The results obtained from this novel approach proved to be quite dramatic. Compared to control "untreated" tumors, where representative sections (7 slides/tumor) obtained outside the central core region revealed nearly 100% viable cells (FIG. 5C), similarly located sections obtained from tumors treated with 3-BrPA (FIG. 5D) contained almost all non-viable cells (nearly 100% necrosis). Viable tumor cells were detected only in small areas near arteries feeding the tumors (FIG. 5E), and at the tumor periphery where sinusoidal blood is available. This may reflect more active mitochondria in these oxygen rich environments that are not completely debilitated at the concentrations of 3-BrPA used. Significantly, no damage occurred to liver tissue surrounding tumors that had been treated with 3-BrPA (FIGS. 5F and 5G).

These results, reproduced in a number of experiments, were subjected to statistical evaluation. Tumors untreated with 3-BrPA (controls) contain 74±5% viable cells in the entire population (FIG. 5H, 1st column). The remaining cells, located within the hypoxic tumor core, have already become non-viable, a common feature of rapidly growing solid tumors. Treatment with a single intraarterial injection of 3-BrPA decreases the number of viable cells to 16±5% (FIG. 5H, 2nd column), thus increasing the total number of non-viable cells in the population to 84±5% (P<0.05). The maximal number of non-viable cells observed in any one experiment was 90%. In sharp contrast, the surrounding liver tissue remained completely viable in all cases examined (FIG. 5H, 3rd and 4th columns).

The portal veins, sinusoids, and bile ducts remained completely intact, with the only apparent damage occurring occasionally in the peribiliary arteriolar complexes at much higher concentrations of 3-BrPA (5 mM). These and the above findings suggest that most of the 3-BrPA injected directly into the tumor remained therein, and if any leakage occurred, most was neutralized by natural reducing agents (e.g., glutathione) present in the surrounding tissue.

Example 18

Figure 6:
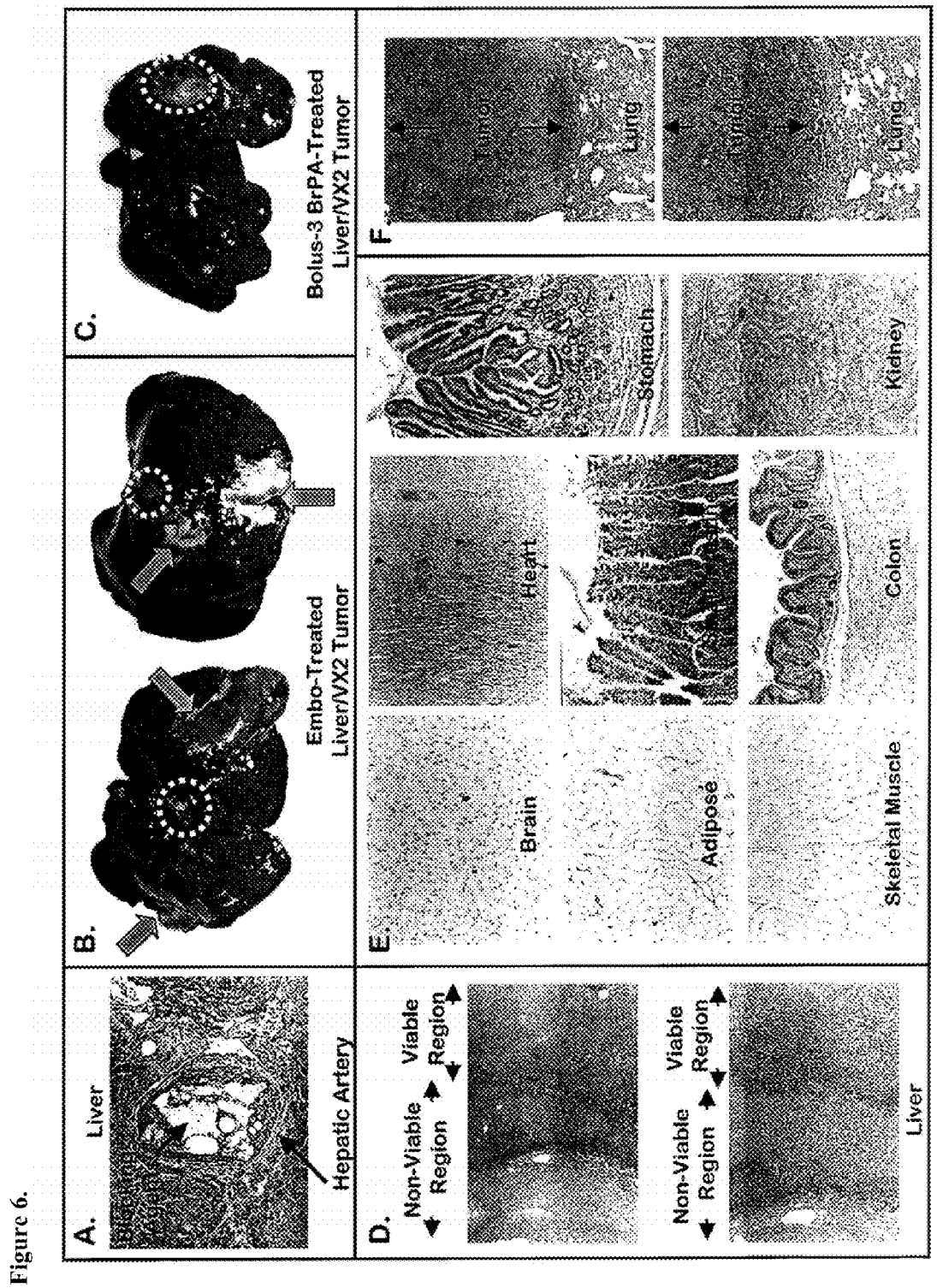
FIG. 6 depicts evidence for the benefits of intraarterial therapy for liver cancer using 3-BrPA over current therapy using embolization.

Conventional Therapy for Advanced Stage Liver Tumors Employing Embolization Results in Significant Damage to Surrounding Liver Tissue We next inquired how this new strategy compares with the approach called "embolization" or "chemoembolization" which is currently used to treat advanced stage liver cancer in humans. Embolization involves blocking the hepatic artery feeding the tumor with a resin-like material mixed with an oil base (e.g., polyvinyl alcohol in Ethiodol), thus depriving the tumor of its oxygen and nutrient sources. Chemoembolization refers to the same procedure but with the inclusion of one or more anticancer agents. Using the same rabbit model, we found that embolization alone of the hepatic artery (FIG. 6A) leading into the VX2 tumor causes such severe damage to the surrounding liver tissue that it is visually evident (FIG. 6B). This is in sharp contrast to the normally appearing liver tissue surrounding VX2 tumors that were not embolized but instead were subjected to direct intraarterial injection of 3-BrPA (FIG. 6C). These findings were further substantiated by histological analyses that revealed extensive non-viable liver tissue surrounding tumors treated by embolization (FIG. 6D), as opposed to only viable tissue surrounding tumors treated by intraarterial injection of 3-BrPA (FIGS. 6F and 6G).

Example 19

The Major Tissues of Animals Bearing 3-BrPA-Treated Liver Tumors Show No Apparent Damage Despite the promising results obtained in support of direct intraarterial injection of 3-BrPA as a therapy for liver cancer, the possibility still existed that 3-BrPA may be damaging other organs. For this reason, 9 major tissues were isolated from animals harboring liver implanted VX2 tumors 4 days after receiving a single intraarterial injection of 3-BrPA. In no case was there evidence for damage to these tissues (FIGS. 6E and 6F). However, the unexpected discovery was made that secondary tumors had developed in the lungs (FIG. 6F), a finding observed also in animals bearing liver implanted tumors that had not been treated with 3-BrPA. As this was a consistent finding (n=6 animals), and because there was no evidence of such tumors in the 8 other major tissues examined, these distant lesions are most likely the result of metastatic spread of the VX2 tumor from the liver to the lung.

Example 20

Figure 7:
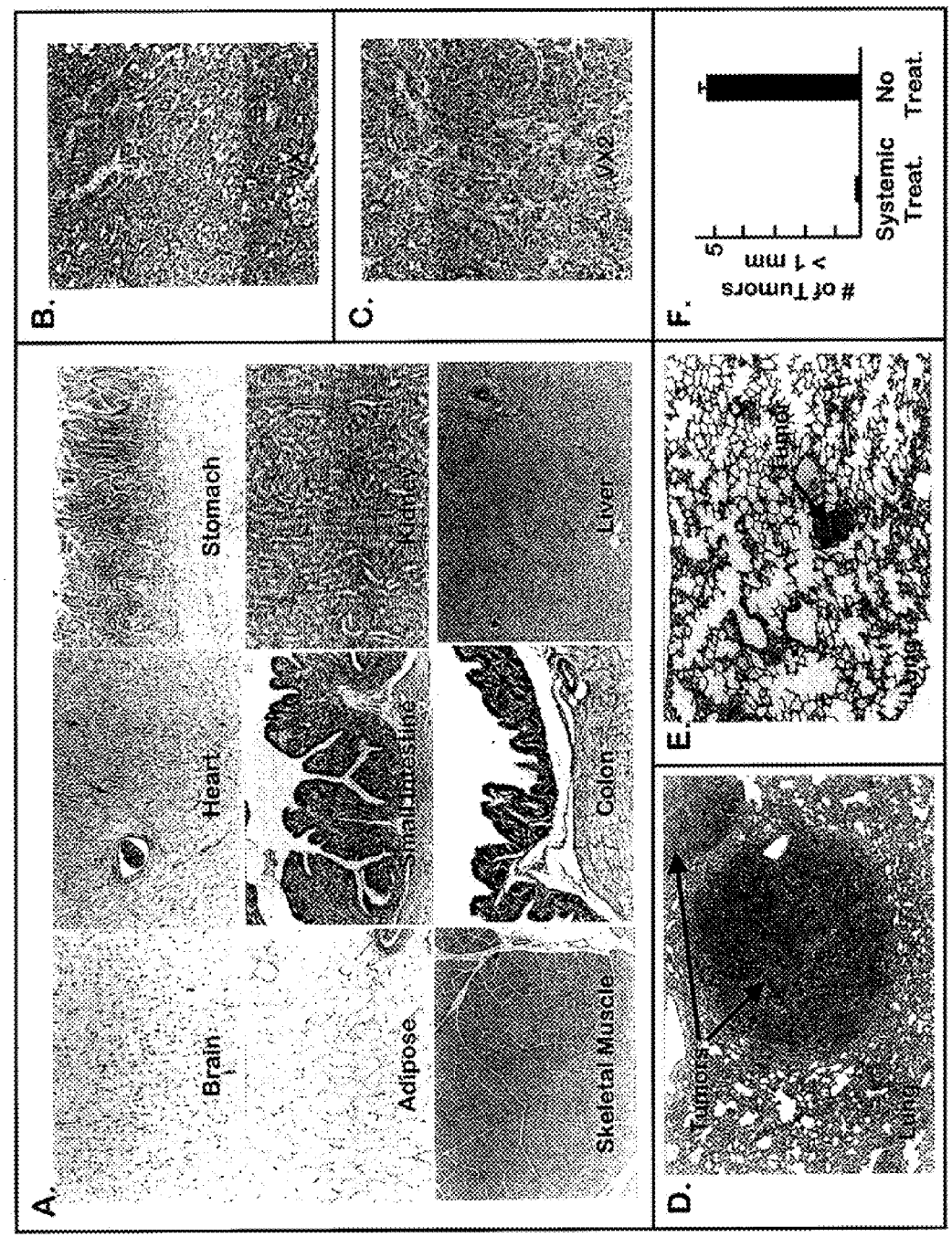
FIG. 7 depicts the effect of systemic delivery of 3-BrPA on animals harboring the liver implanted VX2 tumor.

Systemic Delivery of 3-BrPA Has No Noticeable Effect on the Animals' Health or Behavior and No Effect on Liver Implanted VX2 Tumors, But Does Markedly Suppress the Growth of Metastatic Lung Nodules Finally, it was important to examine the effect of 3-BrPA when delivered systemically (i.e., via the general circulation) on both animal toxicity and its capacity to damage liver implanted tumors. Following delivery of 3-BrPA (25 ml, 0.5 mM) via a marginal ear vein, rabbits that had been harboring liver implanted VX2 tumors for 14 days exhibited normal behavior and, upon sacrifice, histological examination of 9 major tissues revealed no obvious damage (FIG. 7A). Moreover, there was no killing effect on liver implanted VX2 tumors (FIGS. 7B & 7C) as we had observed earlier following direct intraarterial delivery of 3-BrPA (FIGS. 7C & 7D), thus adding further support for this targeted approach as a preferred therapy for liver cancer. However, in sharp contrast to the failure of systemic delivery of 3-BrPA to be therapeutic for liver implanted VX2 tumors (FIGS. 7B & 7C), it was found to be therapeutic for secondary tumors that had developed in the lungs. Interestingly, animals bearing the liver implanted VX2 tumors developed numerous "metastatic" nodules in their lungs, the largest of which were several mm in diameter (FIG. 7D). Most striking in these animals following systemic treatment with 3-BrPA was the finding of only very small tumors (FIG. 7E), and the almost complete disappearance of those with a diameter greater than 1 mm (FIG. 7F).

EQUIVALENTS

The present invention provides, among other things, therapeutic compositions comprising and methods of treating cancer using 3-bromopyruvate and other selective inhibitors of ATP production. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

J. Barnard, et al. (1993) J. Biol. Chem. 268:3654-3661.
Sharma, et al. (2000) Nature Str. Biol. 8:663-668.
M. C. Kew, et al. (1998) In: Feldman, M., et al (eds.) Gastrointestinal and Liver Disease: Pathophysiology, Diagnosis, and Management, pub. W. B. Saunders Co.: 1404-1415.
P. Rous, et al. (1952) J. Exp. Med. 96:159-174.
S. Pauser, et al. (1996) Cancer Res. 56:1863-1867.
J.-F. Geschwind, et al. (2000) JVIR 11: 1245-1255.
M. Sakurai, et al. (1984) Cancer 54:387-392.
M. Soulen, (1994) Oncology 8:77-84.
S. Weinhouse, (1972) Cancer Res. 32:2007-2016.
P. L. Pedersen, (1978) Prog. Exp. Tumor Res. 22:190-274.
E. Bustamante, et al. (1981) J. Biol. Chem. 256:8699-8704.
D. M. Parry, et al. (1983) J. Biol. Chem. 258:10904-10912.
Y. Shinohara, et al. (1991) FEBS Lett. 291:55-57.
A. Rempel, et al. (1996) Cancer Res. 56:2468-2471.
S. P. Mathupala, et al. (1995) J. Biol. Chem. 270:16918-16925.
S. Pilkis, et al. (1994) J. Biol. Chem. 269:21925-21928.
R. A. Harris, (1997) In: T. M. Devlin, (ed.) Textbook of Biochemistry with Clinical Correlations, pub. Wiley-Liss: 267-359.
K. K. Arora, et al. (1988) J. Biol. Chem. 263:14422-14428.

E. F. Greiner, et al. (1994) J. Biol. Chem. 269:31487-31490.
A. Rempel, et al. (1998) Cell Growth and Oncogenesis:3-14.
N. Oya, et al. (1993) J. Nuclear Med. 34:2124-2129.
Liang, T. J., et al. (1993) Hepatology. 18:1326-1333.
El-Serag, H. B. (2001) Clin. Liver Dis. 5:87-107.
El-Serag, H. B., et al. (1999) New Engl. J. Med. 340:745-750.
Saha, S., et al. (2001) Science 294:1343-1346.
Geschwind, J. F., et al. (2000) J. Vasc. Interv. Radiol. 11: 1245-1255.
Venook, A., (1994) J. Clin. Oncol. 12:1323-1334.
Levin, B., et al. (1995) N. Engl. J. Med., 332:1294-1296.
Seong, J., et al. (1999) Intl. J. Rad. Oncol. Biol. Phys. 43:393-397.
Breedis, C., et al. (1954) Am. J. Pathol. 30:969-985.
Pedersen, P. L. (1999) J. Bioenerg. Biomemb. 31:291-304.
Ko, Y. H., et al. (1990) Arch. Biochem. Biophys. 278:373-380.
Ko, Y. H., et al. (2001) Cancer Lett., 173:83-91.
Rous, P., et al. (1952) J. Exp. Med. 96:159-174.
Pauser, S., et al. (1996) Cancer Res. 56:1863-1867.
Weinhouse, S. (1972) G.H.A. Clowes Memorial Lecture. Cancer Res. 32:2007-2016.
Arora, K. K., et al. (1988) J. Biol. Chem. 263:14422-14428.
Meister, A., et al. (1983) Ann. Rev. Biochem. 52:711-760.
Deneke, S. M., et al. (1989) Am. J. Physiol. 257:L163-L173.
Sakurai, M., et al. (1984) Cancer, 54:387-392, 1984.
Soulen, M. (1994) Oncology, 8:77-84, 1994.
US Patent Application 20020068711

We claim:

1. A method of treating a cancerous tumor in a subject comprising administering to the subject an effective amount of 3-bromopyruvate directly to the blood supply of the tumor in the subject via proximal catheterization.

2. The method of claim 1, further comprising administering a second chemotherapeutic agent.

3. The method of claim 2, wherein the second chemotherapeutic agent is selected from the group consisting of: altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin - dunomycin, dexamethosone, doxuribicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

4. The method of claim 1, wherein the tumor is located in a tissue selected from the group consisting of: brain, colon, urogenital, lung, renal, prostate, pancreas, liver, esophagus, stomach, hematopoietic, breast, thymus, testis, ovarian, skin, and uterine tissue.

5. The method of claim 1, further comprising administering a scavenger compound.

6. The method of claim 5, wherein the scavenger compound is selected from the group consisting of: lipoleic acid, glutathione and cysteine.

7. A method of treating a cancerous tumor in a subject comprising administering to the subject an effective amount of a composition represented in general formula:

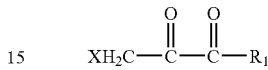

wherein, independently of each occurrence:
X represents bromide;
$R_1$ represents OR, H, N(R")$_2$, C1-C6 alkyl, C6-C12 aryl, C1-C6 heteroalkyl, or C6-C12 heteroaryl;
R" represents H, C1-C6 alkyl, or C6-C12 aryl;
R represents H, alkali metal, C1-C6 alkyl, C6-C12 aryl or C(O)R'; and
R' represents H, C1-C20 alkyl or C6-C12 aryl;
wherein administration of the composition is administered directly to the blood supply of the tumor in the subject via proximal catheterization.

8. The method of claim 7, wherein the tumor is located in a tissue selected from the group consisting of brain, colon, urogenital, lung, renal, prostate, pancreas, liver, esophagus, stomach, hematopoietic, breast, thymus, testis, ovarian, skin, and uterine tissue.

9. The method of claim 7, further comprising administration of a scavenger compound.

10. The method of claim 9, wherein the scavenger compound is selected from the group consisting of: lipoleic acid, glutathione and cysteine.

11. The method of claim 7, further comprising administering a second chemotherapeutic agent.

12. The method of claim 11, wherein the second chemotherapeutic agent is selected from the group consisting of: altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin - dunomycin, dexamethosone, doxuribicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

* * * * *